(12) United States Patent
Dietz et al.

(10) Patent No.: US 10,094,835 B2
(45) Date of Patent: Oct. 9, 2018

(54) TREATING PATIENTS BASED ON IMMUNE SUBTYPES

(71) Applicant: MAYO FOUNDATION FOR MEDICAL EDUCATION AND RESEARCH, Rochester, MN (US)

(72) Inventors: Allan B. Dietz, Chatfield, MN (US); Michael P. Gustafson, Rochester, MN (US); Yi Lin, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 14/889,086

(22) PCT Filed: May 7, 2014

(86) PCT No.: PCT/US2014/037058
§ 371 (c)(1),
(2) Date: Nov. 4, 2015

(87) PCT Pub. No.: WO2014/182761
PCT Pub. Date: Nov. 13, 2014

(65) Prior Publication Data
US 2016/0077096 A1   Mar. 17, 2016

Related U.S. Application Data

(60) Provisional application No. 61/821,655, filed on May 9, 2013.

(51) Int. Cl.
*G01N 33/574* (2006.01)
*A61N 5/10* (2006.01)

(52) U.S. Cl.
CPC ......... *G01N 33/57426* (2013.01); *A61N 5/10* (2013.01); *G01N 33/57407* (2013.01); *G01N 2333/70514* (2013.01); *G01N 2333/70596* (2013.01); *G01N 2800/52* (2013.01)

(58) Field of Classification Search
CPC .................................................. G01N 33/574
USPC ............................................. 424/85.1, 133.1
See application file for complete search history.

(56) References Cited

U.S. PATENT DOCUMENTS

| | | |
|---|---|---|
| 6,376,202 B1 | 4/2002 | Davis |
| 2007/0031443 A1 | 2/2007 | Vaishnaw et al. |
| 2008/0057043 A1 | 3/2008 | Naldini et al. |
| 2009/0074787 A1* | 3/2009 | Gomez-Navarro ........................ A61K 31/404 424/142.1 |
| 2012/0141514 A1 | 6/2012 | Kuehne et al. |
| 2012/0183575 A1 | 7/2012 | Gabrielsson |
| 2012/0230989 A1 | 9/2012 | Dietz |
| 2012/0276004 A1 | 11/2012 | Epstein et al. |

FOREIGN PATENT DOCUMENTS

WO   WO2012138857   10/2012

OTHER PUBLICATIONS

Wood et al. (Journal of Neuro-Oncology, 2000, 48: 113-120).*
Appay et al., "Immuno-monitoring of CD8+ T cells in whole blood versus PBMC samples," *J. Immunol Methods.*, 309(1-2):192-199, Feb. 2006.
Asadullah et al., "Immunodepression following neurosurgical procedures," *Crit Care Med.*, 23(12):1976-1983, Dec. 1995.
Asadullah et al., "Very low monocytic HLA-DR expression indicates high risk of infection—immunomonitoring for patients after neurosurgery and patients during high dose steroid therapy," *Eur J Emerg Med.*, 2(4):184-190, Dec. 1995.
Atzpodien et al., "Adjuvant treatment with interleukin-2- and interferon-alpha2a-based chemoimmunotherapy in renal cell carcinoma post tumour nephrectomy: results of a prospectively randomised trial of the German Cooperative Renal Carcinoma Chemoimmunotherapy Group (DGCIN)," *Br J Cancer.*, 92(5):843-846, Mar. 14, 2005.
Autissier et al., "Evaluation of a 12-color flow cytometry panel to study lymphocyte, monocyte, and dendritic cell subsets in humans," *Cytometry A.*, 77(5):410-419, May 2010.
Axtelle and Pribble, "IC14, a CD14 specific monoclonal antibody, is a potential treatment for patients with severe sepsis," *J Endotoxin Res.*, 7(4):310-314, 2001.
Banham, "Cell-surface IL-7 receptor expression facilitates the purification of FOXP3(+) regulatory T cells," *Trends Immunol.*, 27(12):541-544, Epub Oct. 12, 2006.
Bauer et al., "Accuracy of waste blood measurement in critically ill patients," *Intensive Care Med.*, 37(4):721-722, Epub Jan. 18, 2011.
Bernard et al., "Report of the American-European consensus conference on ARDS: definitions, mechanisms, relevant outcomes and clinical trial coordination. The Consensus Committee," *Intensive Care Med.*, 20(3):225-232, 1994.
Bernard et al., "The American-European Consensus Conference on ARDS. Definitions, mechanisms, relevant outcomes, and clinical trial coordination," *Am. J. Crit. Care Med.*, 149(3):818-824, Mar. 1994.
Cheville et al., "Comparisons of outcome and prognostic features among histologic subtypes of renal cell carcinoma," *Am. J. Surg. Pathol.*, 27(5):612-624, May 2003.
Chow et al., "Rising incidence of renal cell cancer in the United States," *JAMA*, 281(17):1628-1631, May 1999.
Contal and O'Quigley, "An application of changepoint methods in studying the effect of age on survival in breast cancer," *Comput Stat Data Analysis.*, 30(3):253-270, May 28, 1999.
Davis, "A prescription for human immunology," *Immunity*, 29(6):835-838, Dec. 19, 2008.

(Continued)

*Primary Examiner* — Yan Xiao
(74) *Attorney, Agent, or Firm* — Fish & Richardson P.C.

(57) ABSTRACT

This document provides methods and materials for treating patients following an assessment of immune subtypes such as an assessment of peripheral blood phenotypes. For example, methods and materials for treating a mammal having a medical condition after assessing a mammal's level of CD14+/DR− cells (e.g., CD14+/DR− monocytes) and level of CD4+ cells (e.g., CD4+ T cells) and classifying the mammal has being likely to experience a favorable or unfavorable medical outcome based at least in part on the mammal's level of CD14+/DR− cells and level of CD4+ cells are provided.

3 Claims, 11 Drawing Sheets

(56) References Cited

OTHER PUBLICATIONS de Jager et al., "Prerequisites for cytokine measurements in clinical trials with multiplex immunoassays," *BMC Immunol.*, 10:52, Sep. 28, 2009.
Deininger et al., "Expression and release of CD14 in astrocytic brain tumors," *Acta Neuropathol.*, 106(3):271-277, Epub Jun. 27, 2003.
Diaz-Montero et al., "Increased circulating myeloid-derived suppressor cells correlate with clinical cancer stage, metastatic tumor burden, and doxorubicin-cyclophosphamide chemotherapy," *Cancer Immunol Immunother.*, 58(1):49-59, print Jan. 2009, Epub Apr. 2008.
Ege et al., "Prediction of survival using absolute lymphocyte count for newly diagnosed patients with multiple myeloma: a retrospective study," *Br J Haematol*, 141(6):792-798, Jun. 2008.
Filipazzi et al., "Identification of a new subset of myeloid suppressor cells in peripheral blood of melanoma patients with modulation by a granulocyte-macrophage colony-stimulation factor-based antitumor vaccine," *J Clin Oncol.*, 25(18):2546-2553, Jun. 2007.
Gabrilovich and Nagaraj, "Myeloid-derived suppressor cells as regulators of the immune system," *Nat Rev Immunol.*, 9(3):162-174, Mar. 2009.
Getman et al., "Pathologic staging of renal cell carcinoma: significance of tumor classification with the 1997 TNM staging system," *Cancer*, 91:354-361, Jan. 2001.
Gustafson et al., "Association of an increased frequency of CD14+ HLA-DR lo/neg monocytes with decreased time to progression in chronic lymphocytic leukaemia (CLL)," *Br J Haematol.*, 156(5):674-676, Epub Nov. 3, 2011.
Gustafson et al., "Immune monitoring using the predictive power of immune profiles," *J Immunother Cancer.*, 1:7, Jun. 27, 2013.
Gustafson et al., "Systemic immune suppression in glioblastoma: the interplay between CD14+HLA-DRlo/neg monocytes, tumor factors, and dexamethasone," *Neuro Oncol.*, 12(7):631-644, Epub Feb. 23, 2010.
Harton and Ting, "Class II transactivator: mastering the art of major histocompatibility complex expression," *Mol Cell Biol.*, 20(17):6185-6194, Sep. 2000.
Hoechst et al., "A new population of myeloid-derived suppressor cells in hepatocellular carcinoma patients induces CD4(+)CD25(+)Foxp3(+) T cells," *Gastroenterology*, 135(1):234-243, print Jul. 2008 Epub Mar. 2008.
Höflich et al., "Regulatory immunodeficiency and monocyte deactivation Assessment based on HLA-DR expression," *Clinical and Applied Immunology Reviews*, 2(6):337-344, Oct.-Dec. 2002.
Iscimen et al., Risk factors for the development of acute lung injury in patients with septic shock: an observational cohort study, *Crit Care Med.*, 36(5):1518-1522, May 2008.
Iwakami et al., "Granulocyte and monocyte adsorption apheresis therapy modulates monocyte-derived dendritic cell function in patients with ulcerative colitis," *Ther Apher Dial.*, 13(2):138-146, Apr. 2009.
Kiertscher et al., "Tumors promote altered maturation and early apoptosis of monocyte-derived dendritic cells," *J Immunol.*, 164(3):1269-1276, Feb. 2000.
Ko et al., "Sunitinib mediates reversal of myeloid-derived suppressor cell accumulation in renal cell carcinoma patients," *Clin Cancer Res.*, 15(6):2148-2157, Epub Mar. 10, 2009.
Kohrt et al., "Profile of immune cells in axillary lymph nodes predicts disease-free survival in breast cancer," *PLoS Med.*, 2(9):e284, Epub Sep. 6, 2005.
Lin et al., "Immunosuppressive CD14+HLA-DR(low)/-monocytes in B-cell non-Hodgkin lymphoma," *Blood* 117(3):872-881, Jan. 20, 2011, Epub Nov. 9, 2010.
Longo et al., "Single-cell network profiling of peripheral blood mononuclear cells from healthy donors reveals age- and race-associated differences in immune signaling pathway activation," *J Immunol.*, 188(4):1717-1725, Epub. Jan. 13, 2012.
Maas et al., "Immune profiles of pediatric cancer patients," presented at the Society for Immunotherapy of Cancer 2011 Annual Meeting, Nov. 4-6, 2011, 1 page.
Mayo Clinic, ClinicalTrials.gov Identifier: NCT00562328, "Rituximab, Alemtuzumab, and GM-CSF As First-Line Therapy in Treating Patients With Early-Stage Chronic Lymphocytic Leukemia," ClinicalTrials.gov [online] Nov. 21, 2007 [retrieved Oct. 28, 2015]. Retrieved from the Internet: <URL: https://www.clinicaltrials.gov/ct2/show/NCT00562328?term=NCT00562328&rank=1>, 5 pages.
Minniti et al., "Phase II study of short-course radiotherapy plus concomitant and adjuvant temozolomide in elderly patients with glioblastoma," *Int J Radiat Oncol Biol Phys.*, 83(1):93-99, Epub Nov. 11, 2011.
Moore et al., "Postinjury multiple organ failure: a bimodal phenomenon," *J Trauma.*, 40(4):501-510; discussion 510-512, Apr. 1996.
Morimura et al., "Monocyte subpopulations in human gliomas: expression of Fc and complement receptors and correlation with tumor proliferation," *Acta Neuropathol.*, 80(3):287-294, 1990.
Ostrand-Rosenberg and Sinha, "Myeloid-derived suppressor cells: linking inflammation and cancer," *J Immunol.*, 182(8):4499-506, Apr. 2009.
Palmer et al., "Cell-type specific gene expression profiles of leukocytes in human peripheral blood," *BMC Genomics*, 7:115, May 16, 2006.
Peters et al., "Acquired immunoparalysis in paediatric intensive care: prospective observational study," *BMJ.*, 319(7210):609-610, Sep. 1999.
Porrata et al., "Early lymphocyte recovery predicts superior survival after autologous stem cell transplantation in non-Hodgkin lymphoma: a prospective study," *Biology of Blood & Marrow Transplantation*, 14(7):807-816, Jul. 2008.
Rapp et al., "Cellular immunity of patients with malignant glioma: prerequisites for dendritic cell vaccination immunotherapy," *J Neurosurg.*, 105(1):41-50, Jul. 2006.
Rittirsch et al., "Harmful molecular mechanisms in sepsis," *Nat Rev Immunol.*, 8(10):776-787, Oct. 2008.
Schimke et al., "Anti-CD14 mAb treatment provides therapeutic benefit after in vivo exposure to endotoxin," *Proc Natl Acad Sci U S A.*, 95(23):13875-13880, Nov. 1998.
Serafini et al., "Myeloid-derived suppressor cells promote cross-tolerance in B-cell lymphoma by expanding regulatory T cells," *Cancer Res.*, 68(13):5439-5449, Jul. 2008.
Serafini et al., "Phosphodiesterase-5 inhibition augments endogenous antitumor immunity by reducing myeloid-derived suppressor cell function," *J Exp Med.*, 203(12):2691-2702, Nov. 2006.
Sester et al., "Strong depletion of CD14(+)CD16(+) monocytes during haemodialysis treatment," *Nephrol Dial Transplant.*, 16(7):1402-1408, Jul. 2001.
Sinha et al., "Proinflammatory S100 proteins regulate the accumulation of myeloid-derived suppressor cells," *J Immunol.*, 181(7):4666-4675, Oct. 2008.
Soini et al., "Treatment of follicular non-Hodgkin's lymphoma with or without rituximab: cost-effectiveness and value of information based on a 5-year follow-up," *Ann Oncol.*, 22(5):1189-1197, Epub Dec. 6, 2010.
Takeda et al., "MHC class II molecules are not required for survival of newly generated CD4+ T cells, but affect their long-term life span," *Immunity*, 5(3):217-228, Sep. 1996.
Tokunaga et al., "Successful treatment of renal cell carcinoma with mediastinal lymph node metastasis by interleukin-2: a case report," *Tokai J Exp Clin Med.*, 30(2):111-115, Jul. 2005.
van Ravenswaay Claasen, "Tumor infiltrating cells in human cancer. On the possible role of CD16+ macrophages in antitumor cytotoxicity," *Lab Invest.*, 67(2):166-174, Aug. 1992.
Viret and Janeway, "MHC and T cell development," *Rev Immunogenet.*, 1(1):91-104, 1999.
Vuk-Pavlovic et al., "Rebuilding immunity in cancer patients," *Blood Cells Mol Dis.*, 40(1):94-100, print Jan.-Feb. 2008, Epub Sep. 2007.
Webster et al., "Mononuclear cell infiltration in clear-cell renal cell carcinoma independently predicts patient survival," *Cancer*, 107(1):46-53, Jul. 1, 2006.
Xin et al., "Sunitinib inhibition of Stat3 induces renal cell carcinoma tumor cell apoptosis and reduces immunosuppressive cells," *Cancer Res.*, 69(6):2506-2513, print Mar. 2009, Epub Feb. 2009.

(56) References Cited

OTHER PUBLICATIONS

Yu et al., [A study on HLA-Dr expression of brain tumor cells and mononuclear cell subsets infiltrating in these tumors], [Article in Chinese], Zhonghua Bing Li Xue Za Zhi, 23(4):221-223, Aug. 1994, [English abstract only].
Zea et al., "Arginase-producing myeloid suppressor cells in renal cell carcinoma patients: a mechanism of tumor evasion," *Cancer Res.*, 65(8):3044-3048, Apr. 2005.
International Preliminary Report on Patentability for Application No. PCT/US2011/058981, dated May 7, 2013, 4 pages.
International Preliminary Report on Patentability for PCT/US2010/055856, dated May 15, 2012, 5 pages.
International Preliminary Report on Patentability for PCT/US2013/069573, dated May 28, 2015, 13 pages.
International Preliminary Report on Patentability for PCT/US2014/037058, dated Nov. 19, 2015, 6 pages.
International Search Report and Written Opinion for Application No. PCT/US2011/058981, dated Apr. 27, 2012, 5 pages.
International Search Report and Written Opinion for PCT/US2010/055856, dated Aug. 1, 2011, 6 pages.
International Search Report and Written Opinion for PCT/US2013/069573, dated Feb. 27, 2014, 9 pages.
International Search Report and Written Opinion for PCT/US2014/37058, dated Sep. 29, 2014, 7 pages.
U.S. Appl. No. 13/509,089, filed May 10, 2012, Dietz.
U.S. Appl. No. 14/442,465, filed May 13, 2015, Gustafson et al.

\* cited by examiner

Abnormal DRneg= >24.3% (1.5 St. Devs above normal donor average)
Abnormal CD4= 650 cells/ul (1 St. Dev below normal donor average)

Figure 8
A
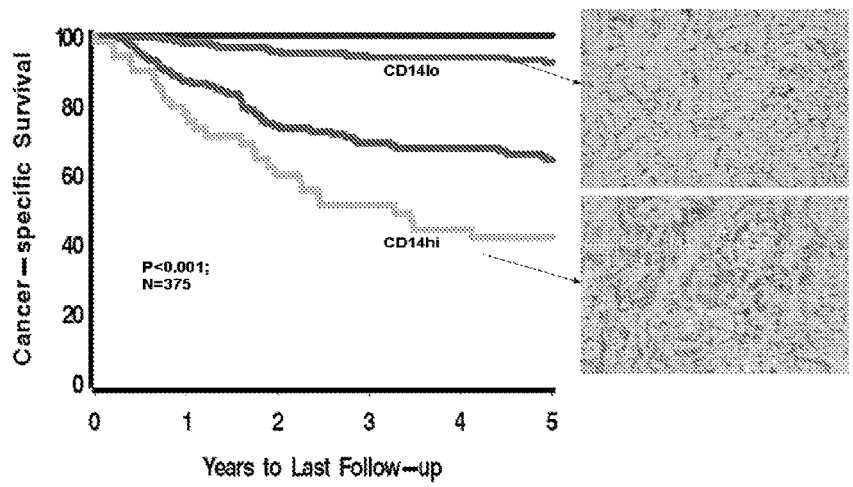
B
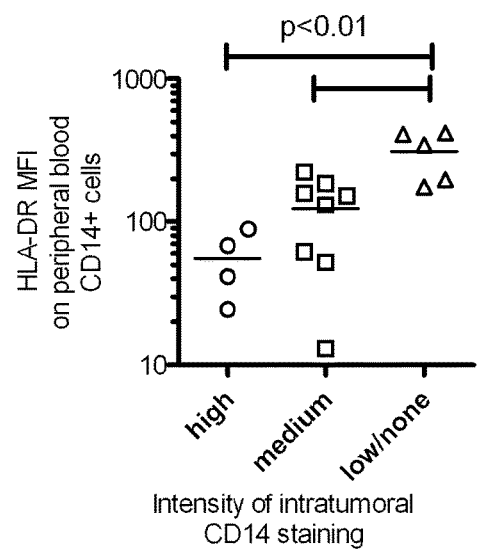

TREATING PATIENTS BASED ON IMMUNE SUBTYPES

CROSS-REFERENCE TO RELATED APPLICATIONS

This application is a National Stage application under 35 U.S.C. § 371 of International Application No. PCT/US2014/037058, having an International Filing Date of May 7, 2014, which claims the benefit of U.S. Provisional Application Ser. No. 61/821,655, filed May 9, 2013. The disclosure of the prior applications are considered part of (and are incorporated by reference in) the disclosure of this application.

BACKGROUND

1. Technical Field

This document relates to methods and materials for treating patients following an assessment of immune subtypes such as an assessment of peripheral blood phenotypes. For example, this document provides methods and materials for treating a mammal having a medical condition after assessing a mammal's level of $CD14^+/DR^-$ cells (e.g., $CD14^+/DR^-$ monocytes) and level of $CD4^+$ cells (e.g., $CD4^+$ T cells) and classifying the mammal has being likely to experience a favorable or unfavorable medical outcome based at least in part on the mammal's level of $CD14^+/DR^-$ cells and level of $CD4^+$ cells.

2. Background Information

The immune system of a mammal is a system of biological structures and processes that helps protect the mammal from diseases by identifying and killing pathogens and tumor cells. A monocyte is one type of white blood cell that is part of the immune system. Monocytes can have several roles in the immune system. For example, monocytes can migrate to sites of infection and differentiate into macrophages and dendritic cells. Another type of cell that is part of the immune system is a $CD4^+$ T cell. $CD4^+$ T cells are a sub-group of lymphocytes that help activate and direct other cells of the immune system.

SUMMARY

This document provides methods and materials for treating patients following an assessment of immune subtypes such as an assessment of peripheral blood phenotypes. For example, this document provides methods and materials for treating a mammal having a medical condition after assessing a mammal's level of $CD14^+/DR^-$ cells (e.g., $CD14^+/DR^-$ monocytes) and level of $CD4^+$ cells (e.g., $CD4^+$ T cells) and classifying the mammal has being likely to experience a favorable or unfavorable medical outcome based at least in part on the mammal's level of $CD14^+/DR^-$ cells and level of $CD4^+$ cells.

As described herein, an appropriate treatment option for a particular medical condition (e.g., cancer, sepsis, autoimmunity, or trauma) can be selected following an assessment of the level of $CD14^+/DR^-$ cells within a mammal. Such an assessment can include, for example, determining the level of $CD14^+/DR^-$ cells within a mammal and comparing the determined values to values of $CD14^+/DR^-$ cells for that particular condition or to values from healthy volunteers to assess whether the level is an altered level (e.g., an increased level of $CD14^+/DR^-$ cells or a complete or substantially complete loss of all $CD14^+/DR^-$ cells). In some cases, the level of $CD4^+$ cells within the mammal can be determined and compared to cut-off values of $CD4^+$ cells for that particular condition or from healthy volunteers to assess whether the level is a normal level, an elevated level (e.g., high level of $CD4^+$ cells), or a reduced level (e.g., low level of $CD4^+$ cells). In some cases, a ratio of the levels of these cells can be calculated with ratios beyond that of normal being used to identify patients at risk. For example, a normal ratio of monocytes ($CD14^+$ cells) to $CD4^+$ T cells (e.g., $CD14^+$ cells per 4 divided by the number of $CD4^+$ T cells per 4) in healthy volunteers can be 0.59±0.29.

An appropriate treatment option for a particular medical condition can be selected based, at least in part, on the normal, elevated, or reduced level of $CD14^+/DR^-$ cells and the normal, elevated, or reduced level of $CD4^+$ cells or ratios thereof. For example, a glioblastoma patient having a normal level of $CD14^+/DR^-$ cells (e.g., <24.3% equal to the mean plus 1.5 standard deviations) and a normal level of $CD4^+$ cells (e.g., >650 cells/4 equal to the mean minus one standard deviation) can be treated by surgery, radiation and/or chemotherapy (e.g., Temodar) under conditions wherein the glioblastoma patient experiences survival greater than 600 days, while a glioblastoma patient having an elevated level of $CD14^+/DR^-$ cells and a reduced level of $CD4^+$ cells can be treated by administering an aggressive treatment (e.g., an investigational therapy) or a combination two or more treatments selected from the following: immunotherapy, treatment with a monocyte activation molecule (e.g., Imiquimod; polyI:C; or TLR ligands), treatment with a monocyte killing agent, a T cell enhancement therapy (allogeneic donor lymphocyte T cells, chimeric antigen receptor (CAR) technology, T cell activation or expansion cytokines such as IL-2, IL15, or IL-23), and treatment with an immune stimulating antibody (e.g., anti-CTLA-4/Ipilimumab or anti-PD1 alone). In some cases, a glioblastoma patient having an elevated level of $CD14^+/DR^-$ cells and a reduced level of CD4 cells can be treated by administering an aggressive treatment or a combination of two or more treatments selected from the following: immunotherapy, treatment with a monocyte activation molecule (e.g., Imiquimod; polyI:C; or TLR ligands), treatment with a monocyte killing agent, a T cell enhancement therapy (allogeneic donor lymphocyte T cells, CAR technology, T cell activation or expansion cytokines such as IL-2, IL15, or IL-23), and treatment with an immune stimulating antibody (e.g., anti-CTLA-4/Ipilimumab or anti-PD1 alone). In some cases, a glioblastoma patient having at least one factor abnormal can be treated by administering, to the glioblastoma patient, an aggressive treatment or a combination of two or more treatments selected from the following: immunotherapy, treatment with a monocyte activation molecule (e.g., Imiquimod; polyI:C; or TLR ligands), treatment with a monocyte killing agent, a T cell enhancement therapy (allogeneic donor lymphocyte T cells, CAR technology, T cell activation or expansion cytokines such as IL-2, IL15, or IL-23), and treatment with an immune stimulating antibody (e.g., anti-CTLA-4/Ipilimumab or anti-PD1 alone).

As another example, a sepsis patient having a reduced level of $CD14^+/DR^-$ cells and an elevated level of CD4 cells can be treated by administering antibiotics, vasopressors, corticosteroids, and/or fluids to the sepsis patient under conditions wherein the sepsis patient is likely to survive, while a sepsis patient having an elevated level of $CD14^+/DR^-$ cells and a reduced level of CD4 cells can be treated by administering, to the sepsis patient, an aggressive treatment or a combination of two or more of the following treatments: a treatment with a monocyte activation molecule (e.g., Imiquimod; polyI:C; TLR ligands), treatment with a monocyte killing agent, a T cell enhancement therapy (e.g., allogeneic donor lymphocyte T cells, CAR technology, T cell activation or expansion cytokines such as IL-2, IL15, or IL-23), and treatment with an immune stimulating antibody (e.g., anti-CTLA-4/Ipilimumab or anti-PD1 alone). A sepsis patient having a reduced level of CD14$^+$/DR$^-$ cells and a reduced level of CD4 cells can be treated by administering, to the sepsis patient, an aggressive treatment or a combination of two or more of the following treatments: a treatment with a monocyte activation molecule (e.g., Imiquimod; polyI:C; TLR ligands), treatment with a monocyte killing agent, a T cell enhancement therapy (e.g., allogeneic donor lymphocyte T cells, CAR technology, T cell activation or expansion cytokines such as IL-2, IL15, or IL-23), and treatment with an immune stimulating antibody (e.g., anti-CTLA-4/Ipilimumab or anti-PD1 alone).

In yet another example, a lymphoma patient (e.g., B-cell non-Hodgkin's lymphoma patient) having a reduced level of CD14$^+$/DR$^-$ cells and either an elevated or reduced level of CD4$^+$ cells can be treated by administering CHOP, R-CHOP, Zevalin, Retuximab, Bexxar, radiation, stem cell transplant, or other lymphoma treatments to the lymphoma patient under conditions wherein the lymphoma patient is likely to survive longer than 750 days, while a lymphoma patient having an elevated level of CD14$^+$/DR$^-$ cells and either an elevated or reduced level of CD4$^+$ cells can be treated by administering an aggressive treatment or a combination of two or more of the following treatments: a treatment with a monocyte activation molecule (e.g., Imiquimod; polyI:C; TLR ligands), treatment with a monocyte killing agent, a T cell enhancement therapy (e.g., allogeneic donor lymphocyte T cells, CAR technology, T cell activation or expansion cytokines such as IL-2, IL15, or IL-23), and treatment with an immune stimulating antibody (e.g., anti-CTLA-4/Ipilimumab or anti-PD1 alone). In some cases, a lymphoma patient having an elevated level of CD14$^+$/DR$^-$ cells and an elevated level of CD4$^+$ cells can be treated by administering (a) a less aggressive treatment to the lymphoma patient than a treatment used to treat a lymphoma patient having an elevated level of CD14$^+$/DR$^-$ cells and a reduced level of CD4$^+$ cells or (b) a combination of two or more of the following treatments: a treatment with a monocyte activation molecule (e.g., Imiquimod; polyI:C; TLR ligands), treatment with a monocyte killing agent, a T cell enhancement therapy (e.g., allogeneic donor lymphocyte T cells, CAR technology, T cell activation or expansion cytokines such as IL-2, IL15, or IL-23), and treatment with an immune stimulating antibody (e.g., anti-CTLA-4/Ipilimumab or anti-PD1 alone).

In another example, the number of CD14$^+$/DR$^-$ cells can correlate to increased numbers of circulating monocytes and circulating granulocytes. Thus, measuring CD14$^+$/DR$^-$ cells can be performed as a substitute for other subtypes.

In some cases, a mammal's likelihood of experiencing either a favorable or unfavorable medical outcome for a particular medical condition can be determined based, at least in part, on the normal, elevated, or reduced level of CD14$^+$/DR$^-$ cells and the normal, elevated, or reduced level of CD4$^+$ cells or ratios thereof. For example, a glioblastoma patient having a normal level of CD14$^+$/DR$^-$ cells (e.g., <24.3% equal to the mean plus 1.5 standard deviations) and a normal level of CD4$^+$ cells (e.g., >650 cells/4 equal to the mean minus one standard deviation) can be classified as being likely to experience a relatively favorable outcome (e.g., survival greater than 600 days), while a glioblastoma patient having a reduced level of CD14$^+$/DR$^-$ cells and a reduced level of CD4$^+$ cells can be classified as being likely to experience a relatively unfavorable outcome (e.g., survival less than 400 days). A glioblastoma patient having an elevated level of CD14$^+$/DR$^-$ cells and a reduced level of CD4$^+$ cells can be classified as being likely to experience a relatively unfavorable outcome (e.g., survival less than 500 days). In some cases, a glioblastoma patient having at least one factor abnormal can be likely to experience an unfavorable outcome (e.g., survival of less than 600 days).

As another example, a sepsis patient having a reduced level of CD14$^+$/DR$^-$ cells and an elevated level of CD4$^+$ cells can be classified as being likely to experience a relatively favorable outcome (e.g., likely to survive), while a sepsis patient having an elevated level of CD14$^+$/DR$^-$ cells and a reduced level of CD4$^+$ cells can be classified as being likely to experience a relatively unfavorable outcome (e.g., greater than 30 percent chance of death). A sepsis patient having a reduced level of CD14$^+$/DR$^-$ cells and a reduced level of CD4$^+$ cells can be classified as being likely to experience a relatively unfavorable outcome (e.g., greater than 10 percent chance of death).

In yet another example, a lymphoma patient (e.g., B-cell non-Hodgkin's lymphoma patient) having a reduced level of CD14$^+$/DR$^-$ cells and either an elevated or reduced level of CD4$^+$ cells can be classified as being likely to experience a relatively favorable outcome (e.g., a likelihood of surviving longer than 750 days), while a lymphoma patient having an elevated level of CD14$^+$/DR$^-$ cells and either an elevated or reduced level of CD4$^+$ cells can be classified as being likely to experience a relatively unfavorable outcome (e.g., a likelihood of not surviving longer than 750 days). In some cases, a lymphoma patient having an elevated level of CD14$^+$/DR$^-$ cells and an elevated level of CD4$^+$ cells can be classified as being likely to experience an slightly more favorable outcome than a lymphoma patient having an elevated level of CD14$^+$/DR$^-$ cells and a reduced level of CD4$^+$ cells.

The methods and materials provided herein can allow clinicians to provide patients with appropriate treatment options and/or appropriate prognostic information about their medical condition. For example, the methods and materials provided herein can be used to identify cancer patients who would potentially benefit from more aggressive forms of treatment when their prognostic subtype is that of a poor outcome.

In general, one aspect of this document features a method for treating cancer. The method comprises, or consists essentially of, (a) detecting the presence of a normal, elevated, or reduced level of CD14$^+$/DR$^-$ cells for the cancer in a mammal having the cancer, (b) detecting the presence of a normal, elevated, or reduced level of CD4$^+$ cells for the cancer in the mammal, and (c) administering a non-immune-based therapy, radiation, chemotherapy, or a combination thereof with or without surgery to the mammal if the mammal is determined to be likely to experience a favorable outcome of the cancer based at least in part on the level of CD14$^+$/DR$^-$ cells and the level of CD4$^+$ cells, or administering, to the mammal, (i) a non-immune-based therapy, radiation, chemotherapy, or a combination thereof with or without surgery and (ii) a T cell stimulating therapy, a CAR therapy, a DLI therapy, a T cell stimulating antibody therapy, an anti-CD14$^+$/HLA-CR$^{neg}$ therapy, a CD14$^+$/DR$^{neg}$ stimulating therapy, a TLR stimulating ligand therapy, a Poly I:C therapy, a CpG therapy, a vaccine therapy, a dendritic cell infusion therapy, a cancer vaccine therapy, a CD14$^+$/DR$^{neg}$ killing strategy therapy, a CD14$^+$/DR$^{neg}$ blocking strategy therapy, a treatment with IDO inhibitors (e.g., NLG8189), a treatment with arginase inhibitors, a treatment with MCSF-R or CSF-R blocking agents, or combinations thereof, if the mammal is determined to be likely to experience an unfavorable outcome of the cancer based at least in part on the level of CD14+/DR− cells and the level of CD4+ cells. The mammal can be a human. The cancer can be glioblastoma or lymphoma. The mammal can have a normal level of CD14$^+$/DR$^-$ cells and a normal level of CD4$^+$ cells, and the method can comprise administering, to the mammal, a non-immune-based therapy, radiation, chemotherapy, or a combination thereof with or without surgery. The mammal can have a reduced level of CD14$^+$/DR$^-$ cells and a reduced level of CD4$^+$ cells, and the method can comprise administering, to the mammal, (i) a non-immune-based therapy, radiation, chemotherapy, or a combination thereof with or without surgery and (ii) a T cell stimulating therapy, a CAR therapy, a DLI therapy, a T cell stimulating antibody therapy, an anti-CD14$^+$/HLA-CR$^{neg}$ therapy, a CD14$^+$/DR$^{neg}$ stimulating therapy, a TLR stimulating ligand therapy, a Poly I:C therapy, a CpG therapy, a vaccine therapy, a dendritic cell infusion therapy, a cancer vaccine therapy, a CD14$^+$DR$^{neg}$ killing strategy therapy, a CD14$^+$/DR$^{neg}$ blocking strategy therapy, a treatment with IDO inhibitors (e.g., NLG8189), a treatment with arginase inhibitors, a treatment with MCSF-R or CSF-R blocking agents, or combinations thereof, if the mammal is determined to be likely to experience an unfavorable outcome of the cancer based at least in part on the level of CD14$^+$/DR$^-$ cells and the level of CD4$^+$ cells.

In another aspect, this document features a method for assessing the likelihood that a mammal having a medical condition will experience a favorable or unfavorable outcome. The method comprises, or consists essentially of, (a) determining whether the mammal has a normal, elevated, or reduced level of CD14$^+$/DR$^-$ cells for the medical condition, (b) determining whether the mammal has a normal, elevated, or reduced level of CD4$^+$ cells for the medical condition, and (c) classifying the mammal as being likely to experience a favorable or unfavorable outcome of the medical condition based at least in part on the level of CD14$^+$/DR$^-$ cells and the level of CD4$^+$ cells. The mammal can be a human. The medical condition can be cancer. The cancer can be glioblastoma. The mammal can have a normal level of CD14$^+$/DR$^-$ cells and a normal level of CD4$^+$ cells, and wherein the method can comprise classifying the mammal as being likely to experience a favorable outcome. The favorable outcome can comprise surviving the glioblastoma for more than 600 days. The mammal can have a reduced level of CD14$^+$/DR$^-$ cells and a reduced level of CD4$^+$ cells, and wherein the method can comprise classifying the mammal as being likely to experience an unfavorable outcome. The unfavorable outcome can comprise surviving the glioblastoma for less than 400 days. The mammal can have an elevated level of CD14$^+$/DR$^-$ cells and a reduced level of CD4$^+$ cells, and wherein the method can comprise classifying the mammal as being likely to experience an unfavorable outcome. The unfavorable outcome can comprise surviving the glioblastoma for less than 500 days. The cancer can be a lymphoma. The mammal can have a reduced level of CD14$^+$/DR$^-$ cells and an elevated or reduced level of CD4$^+$ cells, and wherein the method can comprise classifying the mammal as being likely to experience a favorable outcome. The favorable outcome can comprise surviving the lymphoma for greater than 750 days. The mammal can have an elevated level of CD14$^+$/DR$^-$ cells and an elevated or reduced level of CD4$^+$ cells, and wherein the method can comprise classifying the mammal as being likely to experience an unfavorable outcome. The unfavorable outcome can comprise a likelihood of not surviving the lymphoma for greater than 750 days. The medical condition can be sepsis.

The mammal can have a reduced level of CD14$^+$/DR$^-$ cells and an elevated level of CD4$^+$ cells, and wherein the method can comprise classifying the mammal as being likely to experience a favorable outcome. The favorable outcome can comprise surviving the sepsis. The mammal can have an elevated level of CD14$^+$/DR$^-$ cells and a reduced level of CD4$^+$ cells, and wherein the method can comprise classifying the mammal as being likely to experience an unfavorable outcome. The unfavorable outcome can comprise between 20 and 60 percent chance of death from the sepsis. The mammal can have a reduced level of CD14$^+$/DR$^-$ cells and a reduced level of CD4$^+$ cells, and wherein the method can comprise classifying the mammal as being likely to experience an unfavorable outcome. The unfavorable outcome can comprise having between 5 and 25 percent chance of death from the sepsis.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF THE DRAWINGS

FIG. 8 demonstrates the relationship of the presence of peripheral blood CD14$^+$HLA-DR$^{lo/neg}$ monocytes and intratumoral accumulation of CD14$^+$ cells in renal cell carcinoma. FIG. 8A is a Kaplan-Meier curve of the survival of 375 patients with renal cell carcinoma based on the classification of hi, medium, lo, and no intratumoral staining. FIG. 8B is a graph plotting the correlation of intratumoral CD14 staining and the amount of peripheral blood CD14$^+$HLA-DR$^{neg}$ monocytes from the same patients.

DETAILED DESCRIPTION

Figure 1A:
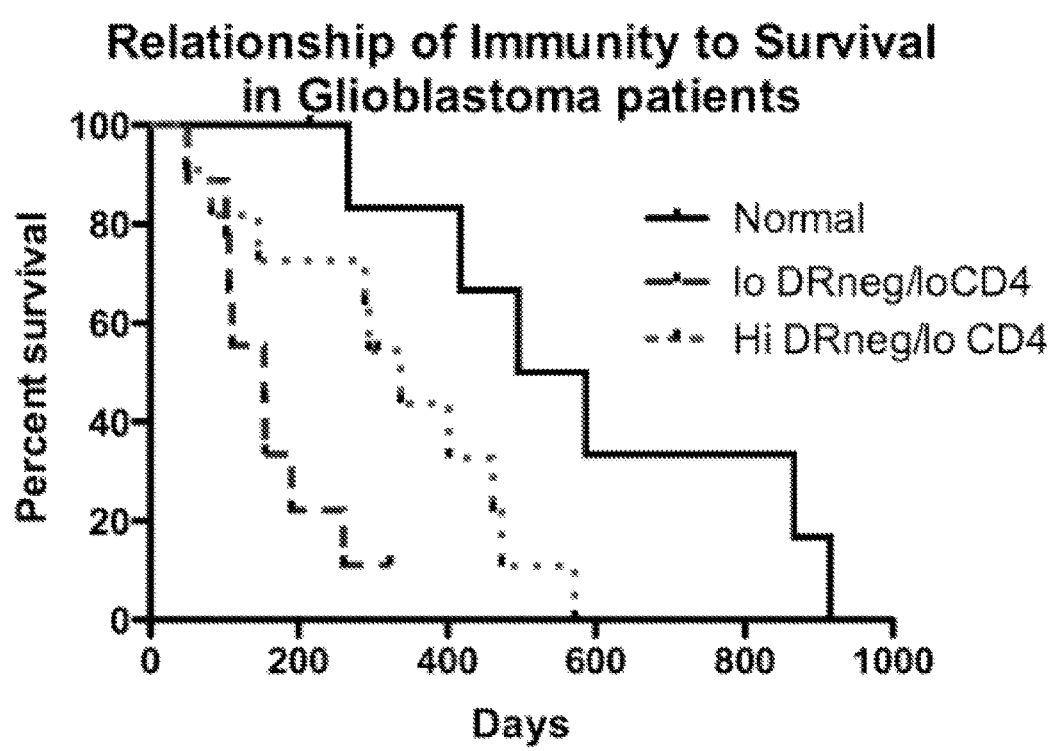
FIG. 1A is a survival curve for glioblastoma patients having (a) normal levels of CD14$^+$/DR$^-$ cells and CD4$^+$ cells, (b) a normal (low) level CD14$^+$/DR$^-$ cells and a reduced level of CD4$^+$ cells, or (c) an elevated level of CD14$^+$/DR$^-$ cells and a reduced level of CD4$^+$ cells.

This document provides methods and materials for treating patients following an assessment of immune subtypes such as an assessment of peripheral blood phenotypes. For example, this document provides methods and materials for treating a mammal having a medical condition after assessing a mammal's level of CD14$^+$/DR$^-$ cells (e.g., CD14$^+$/DR$^-$ monocytes) and level of CD4$^+$ cells (e.g., CD4$^+$ T cells) and classifying the mammal has being likely to experience a favorable or unfavorable medical outcome based at least in part on the mammal's level of CD14$^+$/DR$^-$ cells and level of CD4$^+$ cells.

As described herein, an appropriate treatment option for a particular medical condition (e.g., cancer, sepsis, autoimmunity, or trauma) can be selected following an assessment of the level of CD14$^+$/DR$^-$ cells within a mammal. Such an assessment can include, for example, determining the level of CD14$^+$/DR$^-$ cells within a mammal and comparing the determined values to values of CD14$^+$/DR$^-$ cells for that particular condition or to values from healthy volunteers to assess whether the level is an altered level (e.g., an increased level of CD14$^+$/DR$^-$ cells or a complete or substantially complete loss of all CD14$^+$/DR$^-$ cells). It is noted that healthy volunteers can have an average of about 6% DR$^-$. In cases of immune suppression, this percentage can be higher. In cases of autoimmunity, it can go very low (e.g., virtually all can be DR$^+$).

In addition, the level of CD4$^+$ cells within the mammal can be determined and compared to cut-off values of CD4$^+$ cells for that particular condition or compared to healthy volunteers to assess whether the level is a normal level, an elevated level (e.g., high level of CD4$^+$ cells), or a reduced level (e.g., low level of CD4$^+$ cells). In some cases, a single CD14$^+$/DR$^-$ cell cut-off value can be used to assess whether the level of CD14$^+$/DR$^-$ cells is an elevated level (e.g., a high level of CD14$^+$/DR$^-$ cells) or a reduced level (e.g., a low level of CD14$^+$/DR$^-$ cells) and/or a single CD4$^+$ cell cut-off value can be used to assess whether the level of CD4$^+$ cells is a normal level (e.g., a typical level of CD4$^+$ cells) or a reduced level (e.g., a low level of CD4$^+$ cells). Within particular diseases, the levels for either the CD14$^+$/DR$^-$ or CD4$^+$ cells can be considered as high or extremely high. Once the level of CD14$^+$/DR$^-$ cells and/or the level of CD4$^+$ cells is determined for a mammal having a particular medical condition, the mammal's likelihood of experiencing either a favorable or unfavorable medical outcome for that particular medical condition can be determined based, at least in part, on the normal, elevated, or reduced level of CD14$^+$/DR$^-$ cells by itself or in some cases by the addition of the categorization (e.g., normal, elevated, or reduced level) of CD4$^+$ cells.

The level of CD14$^+$/DR$^-$ cells and/or the level of CD4$^+$ cells can be determined using a sample (e.g., a blood sample) obtained from the mammal to be assessed. Once obtained, the sample can be treated such that the level of CD14$^+$/DR$^-$ cells and the level of CD4$^+$ cells present can be determined. Cell staining and immunofluorescence techniques (e.g., flow cytometry) can be used to determine the level of CD14$^+$/DR$^-$ cells and/or the level of CD4$^+$ cells. For example, anti-CD14, anti-HLA-DR, and anti-CD4 antibodies can be used to perform flow cytometry in order to determine the level of CD14$^+$/DR$^-$ cells and the level of CD4$^+$ cells present within a sample. In some cases, nucleic acid-based assays can be used to assess the level of CD14$^+$/DR$^-$ cells and/or the level of CD4$^+$ cells. For example, the amount of particular transcripts (e.g., CD14, DR, and CD4 transcripts) can be determined in whole blood using techniques such as quantitative PCR. In some cases, the ratios of cells can be used to assess a mammal's (e.g., a human's) peripheral blood phenotype. For example, the ratio of CD14$^+$/DR$^-$ cells to CD4$^+$ cells (or vice versa) can be used as described herein to assess a person's peripheral blood phenotype.

In cases involving patients with glioblastoma, sepsis, or lymphoma, the determined cell levels can be compared to a cut-off value provided herein to determine whether the determined levels are normal, elevated, or reduced. In such cases, determined normal, elevated, or reduced levels can be used as described herein to classify the patient as having a likelihood to experience a favorable or unfavorable outcome. For patients with medical conditions other than glioblastoma, sepsis, or lymphoma, the level of CD14$^+$/DR$^-$ cells and the level of CD4$^+$ cells for a population of similarly afflicted patients with known medical outcomes can be used to identify appropriate cut-off values for the CD14$^+$/DR$^-$ cell and CD4+ cell levels. In addition, the population of patients with known medical outcomes can be used to determine which combinations of cell phenotypes indicate whether a patient is likely to experience a favorable or unfavorable outcome.

Those patients determined to have a favorable or unfavorable outcome as described herein can be treated with a treatment option appropriate for their peripheral blood phenotype. For example, a patient suffering from cancer, sepsis, an autoimmune condition, or trauma who has a normal level of CD4+ cells and a normal level of CD14+/DR− cells can be treated with current medical therapies for the condition to be treated such as non-immune-based therapies, radiation, chemotherapies, and/or surgery. If a patient (e.g., cancer, sepsis, an autoimmune condition, or trauma patient) has a reduced level of CD4+ cells and a normal level of CD14+/DR− cells, then that patient can be treated with both a current medical therapy for the condition to be treated plus a T cell stimulating therapy, a CAR therapy, a DLI therapy (e.g., an allogeneic donor lymphocyte infusion therapy), a T cell stimulating antibody therapy (e.g., treatment with an anti-CTLA-4 antibody, Ipilumimab, or an anti-PD1 antibody), or a combination thereof.

If a patient (e.g., cancer, sepsis, an autoimmune condition, or trauma patient) has a normal or elevated level of CD4+ cells and an elevated level of CD14+/DR− cells, then that patient can be treated with both a current medical therapy for the condition to be treated plus an anti-CD14+/HLA-CR$^{neg}$ therapy, a CD14+/DR$^{neg}$ stimulating therapy, TLR stimulating ligand therapy, a Poly I:C therapy, CpG therapy, vaccine therapy (e.g., BCG or flu vaccine therapy), an allogeneic donor lymphocyte infusion therapy, a dendritic cell infusion therapy, a cancer vaccine therapy, a CD14+/DR$^{neg}$ killing strategy therapy, a CD14+/DR$^{neg}$ blocking strategy therapy, treatment with IDO inhibitors (e.g., NLG8189), treatment with arginase inhibitors, treatment with MCSF-R or CSF-R blocking agents, or combinations thereof.

If a patient (e.g., cancer, sepsis, an autoimmune condition, or trauma patient) has a reduced level of CD4+ cells and an elevated level of CD14+/DR− cells, then that patient can be treated with a current medical therapy for the condition to be treated plus either (a) a T cell stimulating therapy, a CAR therapy, a DLI therapy (e.g., an allogeneic donor lymphocyte infusion therapy), a T cell stimulating antibody therapy (e.g., treatment with an anti-CTLA-4 antibody, Ipilumimab, or an anti-PD1 antibody), or a combination thereof or (b) an anti-CD14+/HLA-CR$^{neg}$ therapy, a CD14+/DR$^{neg}$ stimulating therapy, TLR stimulating ligand therapy, a Poly I:C therapy, CpG therapy, vaccine therapy (e.g., BCG or flu vaccine therapy), an allogeneic donor lymphocyte infusion therapy, a dendritic cell infusion therapy, a cancer vaccine therapy, a CD14+/DR$^{neg}$ killing strategy therapy, a CD14+/DR$^{neg}$ blocking strategy therapy, treatment with IDO inhibitors (e.g., NLG8189), treatment with arginase inhibitors, treatment with MCSF-R or CSF-R blocking agents, or combinations thereof.

The invention will be further described in the following examples, which do not limit the scope of the invention described in the claims.

EXAMPLES

Example 1—The Levels of CD14+/DR− Cells and CD4+ Cells in Glioblastoma Patients can Predict Clinical Outcomes Leukocytes from glioblastoma patients were analyzed by direct antibody staining of whole blood and flow cytometry. The protocol for whole blood staining was performed as described elsewhere (Gustafson et al., *Neuro. Oncol.*, 12: 631-644 (2010)). To assess absolute cell count, 50 μL of whole blood was added and stained in Trucount™ tubes according to the manufacturer's directions (BD Biosciences). Data was acquired on a BD FACSCalibur flow cytometer (Becton Dickinson, Franklin Lakes, N.J.) calibrated the day of use and analyzed with Cell Quest and Multiset (Becton Dickinson) software. The antibodies used included anti-CD14, anti-HLA-DR, and quantitative (Trucount) anti-CD4 antibodies. The peripheral blood monocyte phenotype (e.g., percent DR− cells of CD14+ cells) was plotted against the CD4+ cell count (in cells/μL) to identify cut-off values for glioblastoma patients. The patients were then categorized according to each of these values, and a survival curve was plotted.

In this example, twenty-three glioblastoma patients were phenotyped. Abnormal CD4 counts were defined as one standard deviation below the CD4 counts of normal donors (mean about 983 cells/4 minus one standard deviation of 300=683 cells/μL). A level of CD14+/DR− cells was classified as abnormal if there were two standard deviations above the mean of the normal donor pool (about 25 or greater percent DR− cells of CD14+ cells). This generated four categories:

Normal level of CD4+ cells/normal level of CD14+/DR− cells ("Normal"; See, FIG. 1A);

Low level of CD4+ cells/normal level of CD14+/DR− cells ("lo DRneg, lo CD4"; See, FIG. 1A);

Normal level of CD4+ cells/high level of CD14+/DR− cells (no patients were found with this condition); and Low level of CD4+ cells/high level of CD14+/DR− cells ("hi DRneg lo CD4"; FIG. 1A).

Figure 1B:
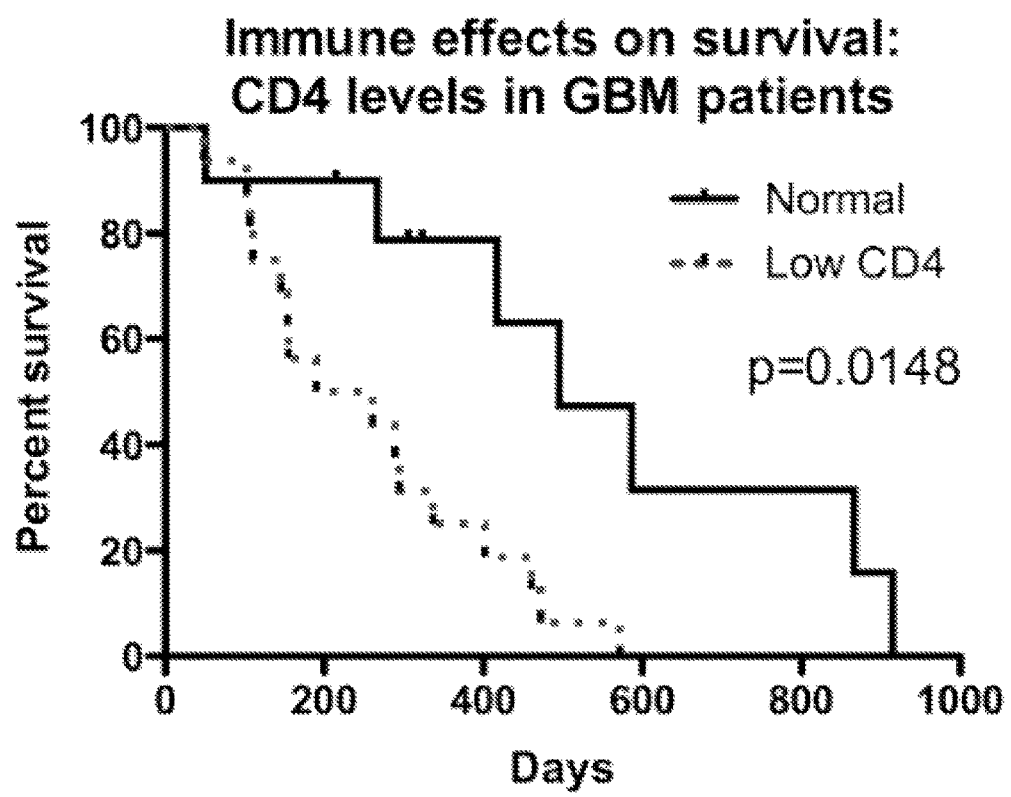
FIG. 1B is a survival curve for glioblastoma patients when plotted based on the CD4$^+$ levels alone.
Figure 1C:
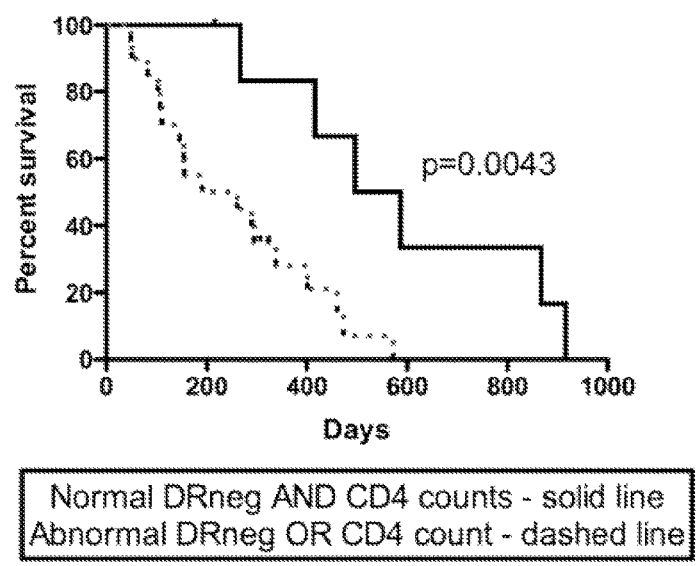
FIG. 1C is a survival curve for glioblastoma comparing patients with either CD4$^+$ or CD14$^+$/DR$^-$ levels at abnormal levels compared to patients with normal values of both.

Glioblastoma patients having normal levels of CD14+/DR− cells and CD4+ cells experience longer survival times than glioblastoma patients in any of the other categories (FIG. 1A-C). These results indicate that measuring immunity using these parameters predicted response to treatment, identified the best (and worst) responses to treatment, and was a useful measure of long term prognosis.

Figure 2:
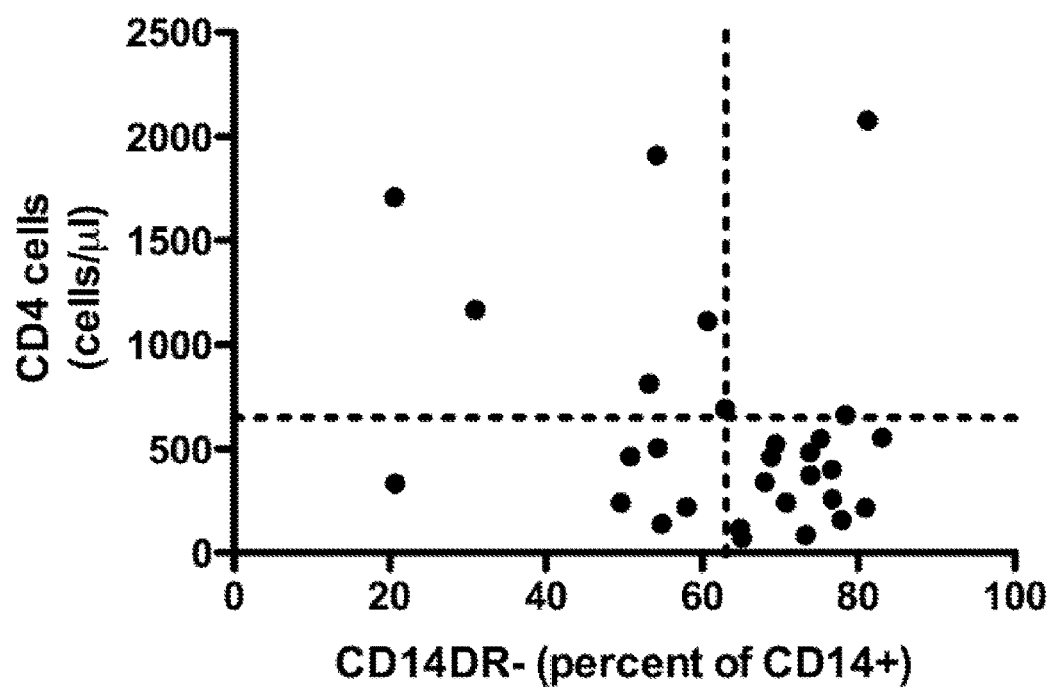
FIG. 2 is a graph plotting the level of CD4$^+$ cells (cells/μL) versus the level of CD14$^+$/DR$^-$ cells (percent of CD14$^+$ cells that are DR$^-$) for sepsis patients. For sepsis patients, the cut off values were 63% DR$^-$ and 650 CD4$^+$ cells/μL.
Figure 3:
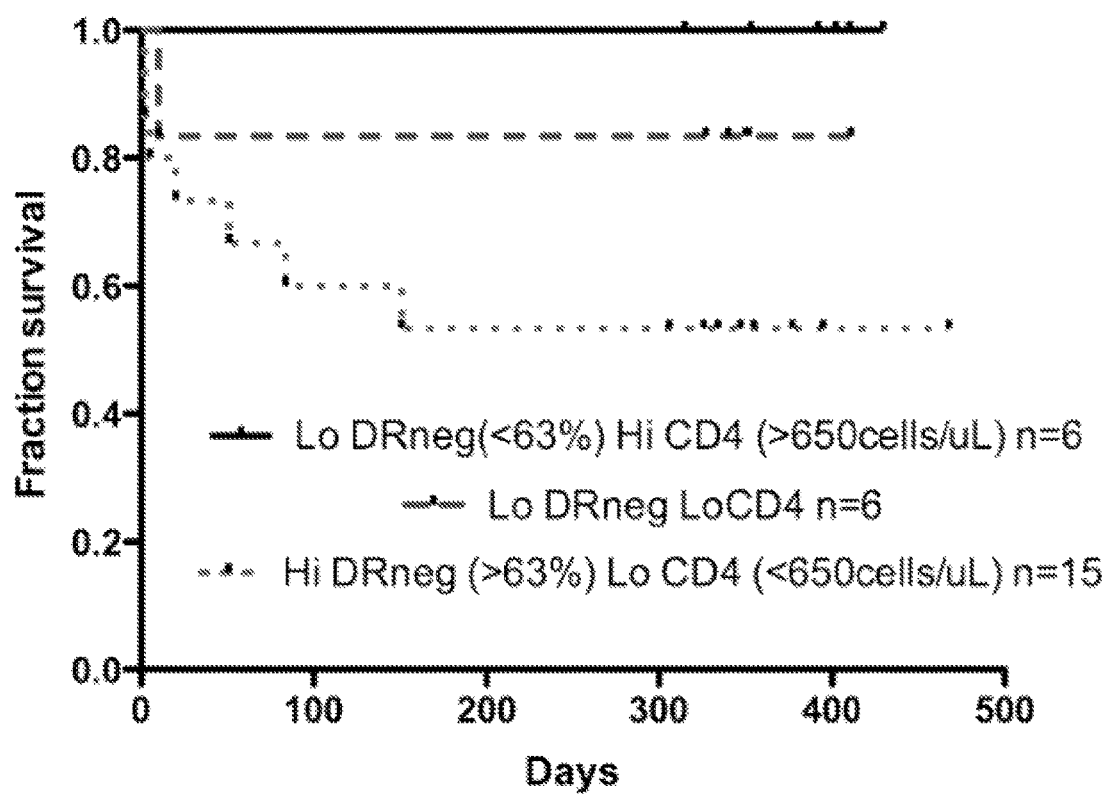
FIG. 3 is a graph plotting percent survival versus days for sepsis with patients grouped on peripheral immunity. Patients were grouped based on normal or elevated levels of CD14$^+$/DR$^-$ cells and normal or reduced levels of CD4$^+$ cells.

Example 2—The Levels of CD14+/DR− Cells and CD4+ Cells in Sepsis Patients can Predict Clinical Outcomes Patients admitted to the intensive care unit with suspicion of bacterial sepsis ("sepsis" patients) were analyzed by direct antibody staining of whole blood and flow cytometry. The protocol for whole blood staining was performed as described elsewhere (Gustafson et al., *Neuro. Oncol.*, 12: 631-644 (2010)). To assess absolute cell count, 50 μL of whole blood was added and stained in Trucount™ tubes according to the manufacturer's directions (BD Biosciences). Data was acquired on a BD FACSCalibur flow cytometer (Becton Dickinson, Franklin Lakes, N.J.) calibrated the day of use and analyzed with Cell Quest and Multiset (Becton Dickinson) software. The antibodies used included anti-CD14, anti-HLA-DR, and quantitative (Trucount) anti-CD4 antibodies. The peripheral blood monocyte phenotype (e.g., percent DR− cells of CD14+ cells) was plotted against the CD4+ cell count (in cells/μL) to identify cut-off values for sepsis patients (FIG. 2). The patients were then categorized according to each of these values, and a survival curve was plotted (FIG. 3).

In this example, twenty-nine patients were phenotyped. A CD4+ cell cut-off value of around 650 (mean=541; median 429) and CD14+/DR− cell cut-off value of about 63% (which happens to be the mean) were used. The levels of CD14$^+$/DR$^-$ cells and CD4$^+$ cells were classified as being elevated or reduced based on these cut-off values.

Sepsis patients having normal levels (for this patient group) of CD14$^+$/DR$^-$ cells and a normal level of CD4$^+$ cells were likely to experience improved survival ("lo DRneg Hi CD4"; FIG. 3). Patients with normal CD14$^+$/DR$^-$ cells and a reduced level of CD4$^+$ cells experienced an increased chance of dying ("Lo DRneg Lo CD4"), while sepsis patients having an elevated level of CD14$^+$/DR$^-$ cells and a reduced level of CD4$^+$ cells ("HiDRneg LoCD4") experienced an increased chance of dying (FIG. 3). There were only two patients with "HiDRneg and HiCD4", and these patients were not included in the analysis.

These results indicate that peripheral blood typing of these two cell types can identify patients likely to survive using current therapy and can used as a tool to identify at risk patients.

Figure 4:
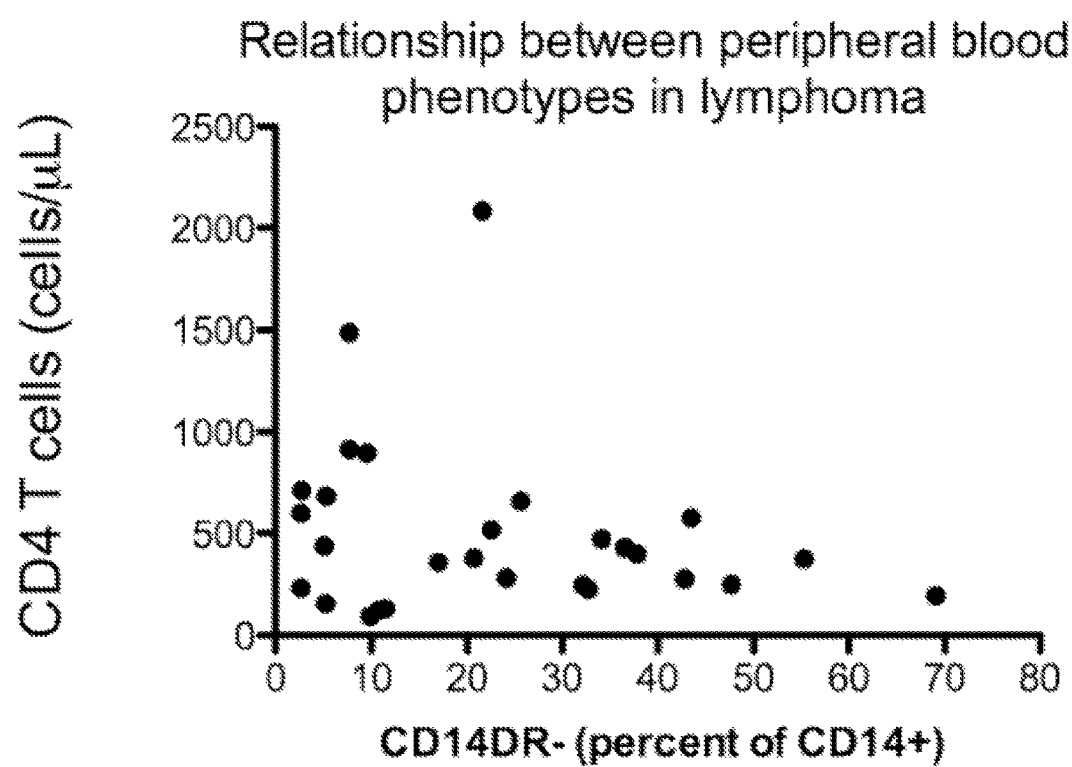
FIG. 4 is a graph plotting the level of CD4$^+$ cells (cells/μL) versus the level of CD14$^+$/DR$^-$ cells (percent of CD14$^+$ cells that are DR$^-$) for lymphoma patients.
Figure 5:
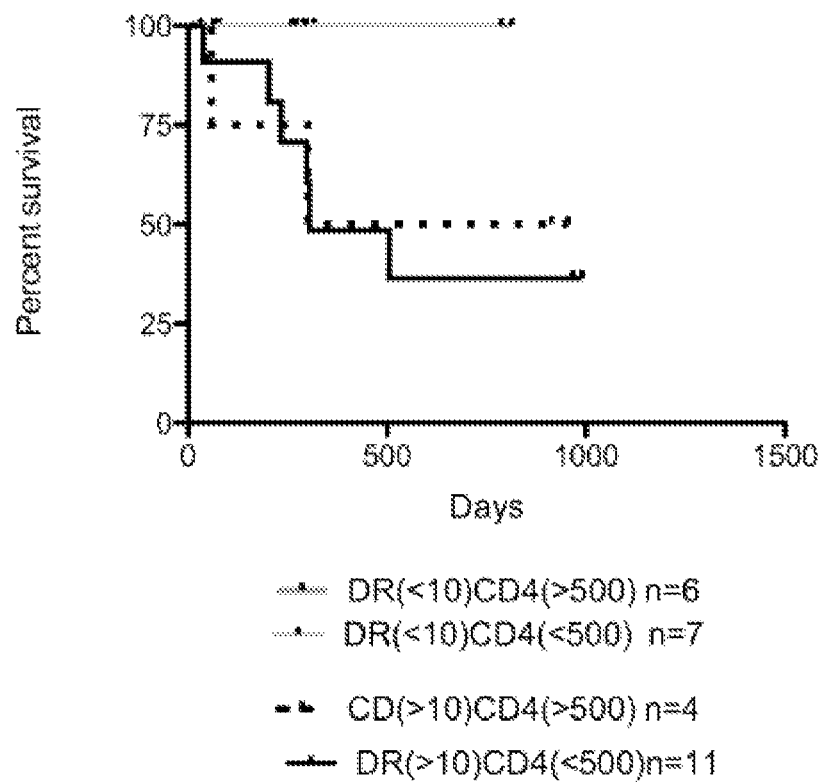
FIG. 5 is a graph plotting overall survival (percent) versus time (days) for lymphoma patients categorized by their peripheral blood phenotype. Patients were grouped according to normal or increased percent of CD14$^+$/DR$^-$ cells and reduced or normal levels of CD4$^+$ cells. The normal (DR (<10%) and normal CD4 (>500 cells/μL)) and the normal DR and low CD4 groups overlap on the survival curve.
Figure 6:
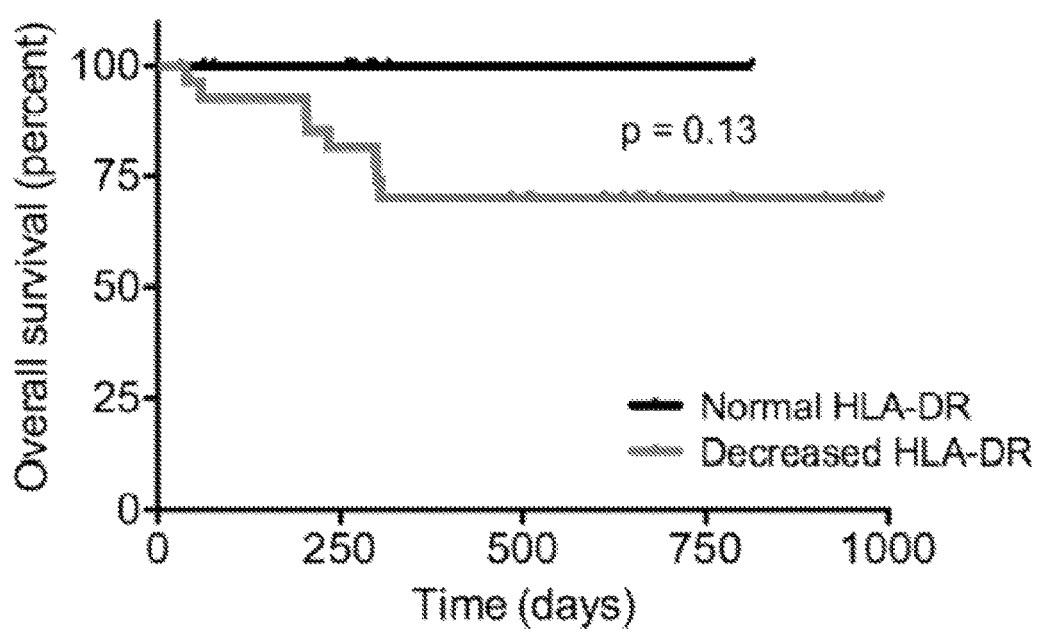
FIG. 6 is a graph plotting the overall survival (percent) versus time (days). The black line represents patients whose monocytes had normal HLA-DR expression (n=11; CD14$^+$ HLA-DR$^{low/neg}$<10% of CD14$^+$ monocytes). The gray line represents patients whose monocytes had a loss of HLA-DR expression (n=29; CD14$^+$HLA-DR$^{low/neg}$ monocytes; monocytes where >10% of CD14$^+$ monocytes had lost HLA-DR expression.

Example 3—The Levels of CD14$^+$/DR$^-$ Cells and CD4$^+$ Cells in Lymphoma Patients can Predict Clinical Outcomes Leukocytes from lymphoma patients were analyzed by direct antibody staining of whole blood and flow cytometry. The protocol for whole blood staining was performed as described elsewhere (Gustafson et al., *Neuro. Oncol.*, 12: 631-644 (2010)). To assess absolute cell count, 50 μL of whole blood was added and stained in Trucount™ tubes according to the manufacturer's directions (BD Biosciences). Data was acquired on a BD FACSCalibur flow cytometer (Becton Dickinson, Franklin Lakes, N.J.) calibrated the day of use and analyzed with Cell Quest and Multiset (Becton Dickinson) software. The antibodies used included anti-CD14, anti-HLA-DR, and quantitative (Trucount) anti-CD4 antibodies. The peripheral blood monocyte phenotype (e.g., percent DR$^-$ cells of CD14$^+$ cells) was plotted against the CD4$^+$ cell count (in cells/μL) to identify cut-off values for lymphoma patients (FIG. 4). The patients were then categorized according to each of these values, and survival curves were plotted (FIGS. 5 and 6).

In this example, twenty-eight lymphoma patients were phenotyped. A CD4$^+$ cell cut-off value of around 500 and CD14$^+$/DR$^-$ cell cut-off value of about 10% were used. The levels of CD14$^+$/DR$^-$ cells and CD4$^+$ cells were classified as being elevated or reduced based on these cut-off values.

Lymphoma patients having an increased level of CD14$^+$/DR$^-$ cells were likely to experience death sooner than patients with normal levels ("Normal" is normal levels of CD14$^+$DR$^-$; "decreased DR" means loss of DR expression on CD14 or equivalent to increased CD14$^+$DR$^-$; FIG. 6). When patients were subgrouped to include reduced or normal levels of CD4, the survival curves were only marginally changed.

These results indicate that in relapsed lymphoma patients, those patients most at risk of progression can be identified using peripheral blood phenotyping.

Example 4—An Increased Frequency of CD14$^+$/HLA-DR$^{low/neg}$ Monocytes Correlates with Decreased Time to Progression in Chronic Lymphocytic Leukemia (CLL)

Figure 7:
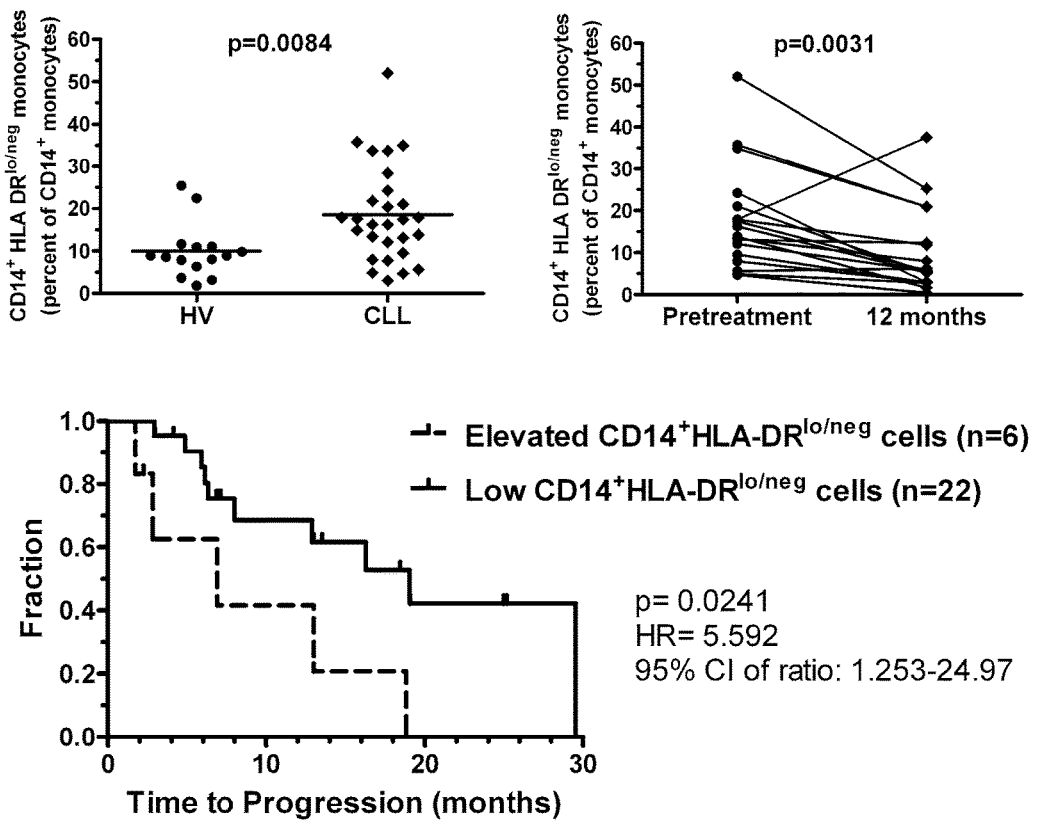
FIG. 7 contains graphs plotting the levels of CD14$^+$HLA-DR$^{neg}$ monocytes in chronic lymphocytic leukemia (CLL). Blood from 29 CLL patients and 15 healthy volunteers were used for immune phenotyping. There was no age difference (median of 58 vs. 59 years, respectively; p=0.2896). Patients were eligible for the clinical trial (ClinicalTrials.gov NCT00562328) if diagnosed with previously untreated high risk CLL using standard criteria and did not meet guidelines for conventional treatment. Blood was collected before initiation of treatment and 6, 9, and 12 months after completion of treatment in patients who had a sustained response. The percent of CD14$^+$ cells with a loss of HLA-DR staining was determined and compared between CLL patients and healthy volunteers (HV; upper left). CLL patients with a sustained response to treatment had a decrease in the frequency of HLA-DR$^{lo/neg}$CD14$^+$ monocytes 12 months after completion of treatment (diamonds) compared to measurement prior to treatment (upper right). Kaplan-Meyer survival curve comparing CLL patients with elevated ratios (>2.5 standard deviations) of CD14$^+$HLA-DR$^{lo/neg}$ monocytes when compared to healthy volunteers (dashed line) or with ratios similar to those seen in healthy volunteers (solid line; bottom panel).

To identify potential monocyte alterations by CLL in patients, flow cytometric analysis of peripheral blood leukocytes in patients (Table 1) with previously untreated early to intermediate stage CLL prior to therapy on a clinical trial of a therapy consisting of a five-week regimen of alemtuzumab, rituximab, and GM-CSF was performed, and their progress was followed through twelve months (ClinicalTrials.gov NCT00562328). Antibody staining of whole blood and flow cytometry data collection were performed as described elsewhere (Gustafson et al., *Neuro. Oncol.*, 12:631-644 (2010)). In healthy individuals, about 90% of circulating CD14$^+$ monocytes were positive for surface HLA-DR. The percentage of leukocytes that were monocytes in CLL patients were similar to those seen in healthy volunteers. However, the CD14$^+$ monocytes in CLL patients were more likely to have reduced staining for HLA-DR than age-matched healthy volunteers (16.8%±11.5% vs. 9.9%±6.4%, p=0.008) (FIG. 7). The expression of monocyte activation markers CD16, TNFR2, and CD80 were similar in the CLL patients and healthy volunteers. However, CD86 expression on monocytes was decreased in CLL patients versus healthy volunteers (83.9%±17.0%; n=9 vs. 94.9%±1.2%; n=5; p=0.0290). The diminished expression of HLA-DR and CD86 molecules suggested that the monocytes in CLL patients could have decreased antigen presenting capacity with reduced immune stimulatory capacity.

TABLE 1

| Patient Characteristics. | |
|---|---|
| Age, median (range) | 59.0 (42.0-77.0) |
| Gender | |
| Female | 8 (27.6%) |
| Male | 21 (72.4%) |
| Follow up Status | |
| Alive | 28 (96.5%) |
| Dead | 1 (3.5%) |
| Median Follow-up (months) | 26.8 (10.1-38.8) |
| Progression Status | |
| No progression | 11 (37.9%) |
| Progression | 18 (62.1%) |
| Rai Stage | |
| 0 | 2 (6.9%) |
| 1 | 23 (79.3%) |
| 2 | 4 (13.8%) |
| CD38+ Expression | |
| Positive | 14 (48.3%) |
| Negative | 15 (51.7%) |
| IgVH Mutation | |
| Mutated | 3 (10.3%) |
| Unmutated | 26 (89.7%) |
| Zap-70 Expression | |
| Positive | 21 (75%) |
| Negative | 7 (25%) |
| FISH, abnormal (24, 82.8%) | |
| 13q14 | 4 (13.8%) |
| 12+ | 6 (20.7%) |
| 11q22 | 10 (34.5%) |
| 17p13 | 3 (10.3%) |
| Other | 1 (3.5%) |
| Normal | 5 (17.2%) |

The relationship between the pre-treatment monocytes, CD14$^+$HLA-DR$^{lo/neg}$ cells, and CD19$^+$ B cell (predominantly CLL cells) counts was also studied. For these comparisons, the percentage of CD14$^+$HLA-DR$^{lo/neg}$ cells or monocytes was converted into cells/μL. A positive correlation between the numbers of B cell and monocyte (p<0.0001) and increased numbers of CD14+HLA-DR$^{neg}$ cells (p=0.0009) was identified. It was investigated whether a sustained reduction in the absolute B cell count after treatment would be associated with a normalization of the immune profile in terms of the monocyte pool. In patients who were in sustained remission at 12 months after completion of therapy (n=18), the median frequency of CD14+HLA-DR$^{lo/neg}$ monocytes decreased (17.9%±12.3% pre-treatment vs. 9.9%±10.0% post-treatment, p=0.0046, FIG. 7; upper right) to a value similar to healthy volunteers. This was not due to selection bias as there was no difference between the pretreatment frequency of CD14+HLA-DR$^{lo/neg}$ monocytes in patients with a sustained 12 month response compared to patients without this response. These results supported a model also observed in glioblastoma of tumor mediated changes in monocyte phenotype and suggest that loss of the tumor signal may lead to reversion to a normal phenotype.

To determine if monocyte phenotypes were prognostic, the time to disease progression in patients with elevated pretreatment frequency of CD14+HLA-DR$^{lo/neg}$ monocytes (≥2.5 standard deviations above the healthy volunteer mean) was compared to those with lower levels of CD14+HLA-DR$^{lo/neg}$ monocytes. The 6 patients with higher CD14+HLA-DR$^{lo/neg}$ monocytes exhibited a shorter time to disease progression (median 6.9 months) compared to 19.1 months for patients with lower levels (n=22; p=0.024, FIG. 7; lower panel). The number of total monocytes did not influence time to disease progression. These data suggest loss of DR expression by CD14 cells is predictive of poorer prognosis.

CD14+HLA-DR$^{lo/neg}$ cells mediate immunosuppression through secretion of IL-10 and/or TGF-β, can induce T regulatory populations, inhibit responder T cells, and have defects in dendritic cell maturation. There is also growing evidence that 'nurse-like cells' are derived from CD14+ cells. Monocytes likely play a dual role in CLL of promoting CLL survival and mediating CLL-induced immunosuppression reflecting the importance of myeloid cell interaction on the pathogenesis of CLL. The elevated frequency of CD14+HLA-DR$^{lo/neg}$ monocytes and their association with increased tumor burden and poorer prognosis suggested an important role of monocytes in the pathogenesis of CLL. Taken together, these results demonstrate that the level of CD14+HLA-DR$^{lo/neg}$ monocytes can be used to determine prognosis and potentially classify patients into various risk groups.

Example 5—An Increased Frequency of Peripheral Blood CD14+HLA-DR$^{low/neg}$ Monocytes Correlates with Increase CD14+ Tumor Infiltration and Poorer Prognosis in Renal Cell Carcinoma The following was performed to assess the associations of tumor CD14 expression with clinical and pathologic features and patient outcome using a large cohort (n=375) of ccRCC patients. The association of maximal intratumoral and peritumoral CD14 expression with cancer-specific survival is illustrated in FIG. 8A. At last follow-up, 159 patients had died, including 100 who died from RCC at a mean of 2.3 years following surgery (median 1.7; range 0-9). Among the 216 patients who were still alive at last follow-up, the mean duration of follow-up was 7.1 years (median 7.3; range 0-10); only 5 (2.3%) patients had fewer than 2 years of follow-up. Estimated cancer-specific survival rates (95% CI, number still at risk) at 1, 3, 5, and 7 years following surgery were 91.0% (88.1-94.0; 328), 79.0% (74.9-83.4; 268), 75.3% (70.9-80.0; 232), and 71.9% (67.3-77.0; 136), respectively. Univariately, patients whose tumors contained moderate CD14 expression were nearly 5 times more likely to die from RCC compared with patients whose tumors contained absent/focal CD14 expression (HR 4.79; p<0.001). Patients whose tumors contained marked CD14 expression were over 11 times more likely to die from RCC compared with patients whose tumors contained absent/focal CD14 expression (HR 11.51; p<0.001). These associations also were evaluated in a multivariable setting adjusting for the SSIGN score. After accounting for the association between SSIGN score and death from RCC, the HRs for the associations of moderate and marked CD14 expression with death from RCC were 2.87 (p<0.001) and 3.03 (p<0.001), respectively. After further adjustment for age at surgery, gender, symptoms at presentation, sarcomatoid differentiation, and the SSIGN score, the HRs for the associations of moderate and marked CD14 expression with death from RCC were 2.53 (95% CI 1.45-4.42; p=0.001) and 2.69 (1.44-5.01; p=0.002), respectively. Since it is technically difficult to assess changes in HLA-DR levels by immunohistochemistry, the tumors were stained for CD14 from the 23 ccRCC patients that were immunophenotyped for CD14 and HLA-DR. It was found that the HLA-DR expression on peripheral blood CD14+ monocytes in ccRCC patients inversely correlated with the intensity of CD14 staining in their corresponding tumors (FIG. 8B). Taken together, these results reveal that the level of peripheral blood CD14+HLA-DR$^{lo/neg}$ monocytes can be a surrogate measure of the amount of CD14+ monocytes in the tumor and that their presence in tumors predicts patient survival.

Example 6—HLA-DR Protein Expression Correlates with HLA-DR mRNA Expression

Figure 9:
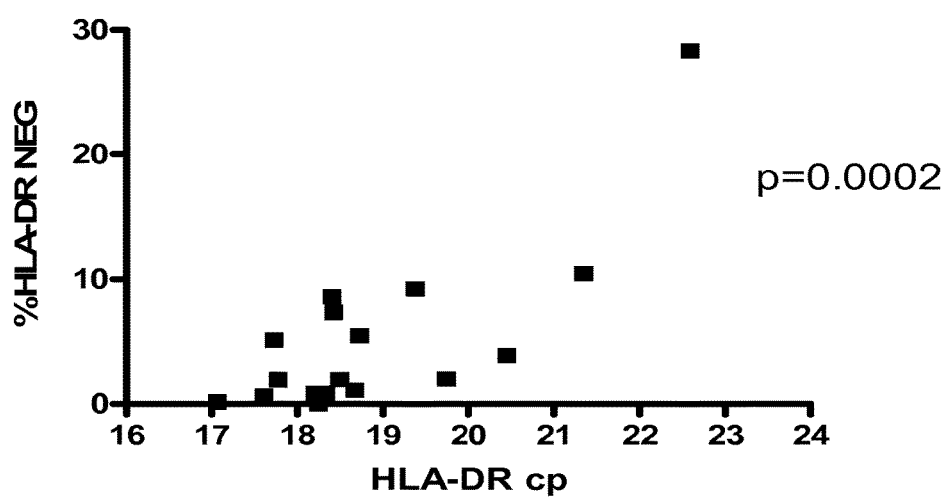
FIG. 9 is a graph plotting flow cytometry and Q-PCR data for HLA-DR expression. Blood samples from healthy volunteers and cancer patients were stained for CD14 and HLA-DR. RNA was isolated from CD14$^+$ populations from the same individuals. Quantitative RT-PCR was performed to determine the level of expression by assessing the crossing point (Cp) of each PCR reaction. The percentage of CD14$^+$HLA-DR$^{lo/neg}$ monocytes were then plotted against the Cp of each PCR reaction.

Paired blood samples from healthy volunteers and cancer patients were analyzed by flow cytometry and quantitative PCR (QPCR). RNA was isolated using the Qiagen RNeasy Plus kit. cDNA and QPCR with TAQMAN probes were performed and analyzed via the Roche Light Cycler 2.0 System. Primers were designed via Roche online tools. Crossing Point (CP) is the threshold in which a gene detected above background. For flow cytometry, cells were stained with appropriate antibodies at RT for 15 minutes, washed in PBS, and fixed in 4% paraformaldehyde. Data were acquired on a FACS Calibur Flow Cytometer and analyzed using CellQuest software. The percentage of CD14+HLA-DR$^{lo/neg}$ monocytes was plotted against the crossing point of HLA-DR expression from each individual (FIG. 9).

Taken together, these results demonstrate that there is a significant correlation between HLA-DR surface expression and transcript amounts suggesting that Q-PCR may be used as an interchangeable technique to flow cytometry in the understanding of the immune biology.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for treating cancer, wherein said method comprises:
    (a) detecting the presence of an elevated level of $CD14^+/DR^-$ cells for said cancer in a mammal having said cancer,
    (b) detecting the presence of a reduced level of $CD4^+$ cells for said cancer in said mammal, and
    (c) administering, to said mammal, (i) a chemotherapy with or without surgery and (ii) an anti-CTLA-4 antibody, Ipilumimab, or an anti-PD1 antibody.

2. The method of claim 1, wherein said mammal is a human.

3. The method of claim 1, wherein said cancer is glioblastoma or lymphoma.

* * * * *

UNITED STATES PATENT AND TRADEMARK OFFICE
CERTIFICATE OF CORRECTION

PATENT NO. : 10,094,835 B2
APPLICATION NO. : 14/889086
DATED : October 9, 2018
INVENTOR(S) : Allan B. Dietz, Michael P. Gustafson and Yi Lin Page 1 of 1

It is certified that error appears in the above-identified patent and that said Letters Patent is hereby corrected as shown below:

In the Claims

In Claim 1, Column 15, Line 11 delete "Ipilumimab," and insert -- Ipilimumab, --, therefor.

Signed and Sealed this
Fifth Day of March, 2019

Andrei Iancu
*Director of the United States Patent and Trademark Office*